United States Patent
Uber, III et al.

(10) Patent No.: US 10,589,018 B2
(45) Date of Patent: Mar. 17, 2020

(54) MULTI-DOSE DISPOSABLE SYSTEM

(71) Applicant: Bayer HealthCare LLC, Whippany, NJ (US)

(72) Inventors: Arthur E. Uber, III, Pittsburgh, PA (US); Ralph H. Schriver, Tarentum, PA (US); Barry L. Tucker, Verona, PA (US); James A. Dedig, Pittsburgh, PA (US)

(73) Assignee: BAYER HEALTHCARE LLC, NJ (US)

( * ) Notice: Subject to any disclaimer, the term of this patent is extended or adjusted under 35 U.S.C. 154(b) by 690 days.

(21) Appl. No.: 15/119,467

(22) PCT Filed: Feb. 18, 2015

(86) PCT No.: PCT/US2015/000027
§ 371 (c)(1),
(2) Date: Aug. 17, 2016

(87) PCT Pub. No.: WO2015/126526
PCT Pub. Date: Aug. 27, 2015

(65) Prior Publication Data
US 2017/0049955 A1    Feb. 23, 2017

Related U.S. Application Data

(60) Provisional application No. 61/941,153, filed on Feb. 18, 2014.

(51) Int. Cl.
*A61M 5/00* (2006.01)
*A61M 5/14* (2006.01)
(Continued)

(52) U.S. Cl.
CPC .......... *A61M 5/007* (2013.01); *A61M 5/1408* (2013.01); *A61M 5/1413* (2013.01);
(Continued)

(58) Field of Classification Search
CPC .. A61M 5/007; A61M 5/1408; A61M 5/1413; A61M 39/223; A61M 1/367; A61M 1/36
See application file for complete search history.

(56) References Cited

U.S. PATENT DOCUMENTS

| | | | | |
|---|---|---|---|---|
| 5,569,208 A | * | 10/1996 | Woelpper | A61M 5/007 604/183 |
| 7,540,854 B2 | * | 6/2009 | Trombley, III | A61M 5/142 600/431 |

(Continued)

FOREIGN PATENT DOCUMENTS

| | | |
|---|---|---|
| WO | 8303538 A1 | 10/1983 |
| WO | 2004006994 A1 | 1/2004 |

OTHER PUBLICATIONS

"Extended European Search Report from EP Application No. 15752177", dated Feb. 5, 2018.

*Primary Examiner* — Nathan R Price
*Assistant Examiner* — Melissa A Snyder
(74) *Attorney, Agent, or Firm* — James R. Stevenson; Bojan Popovic

(57) ABSTRACT

A multi-dose disposable fluid delivery system includes at least one fluid container, a multi-use fluid path set, and a plurality of single-use fluid path sets. The at least one fluid container has a connection port configured for fluidly connecting with a first end of the multi-use fluid path set. The second end of the multi-fluid path set is configured for fluidly connecting to a fluid injection apparatus. The plurality of single-use fluid path sets is connected in sequence to define a fluid path extending from a first single-use fluid path set to a last single- use fluid path set. Each of the plurality single-use fluid path sets has a first end and a second end. The first end of the first single-use fluid path set is configured for connecting to a delivery line. The second end of the last single-use fluid path set is configured for connecting to the injection apparatus.

12 Claims, 13 Drawing Sheets

(51) Int. Cl.
*A61M 5/142* (2006.01)
*A61M 5/145* (2006.01)
*A61M 39/22* (2006.01)
*A61M 39/24* (2006.01)
*A61M 39/26* (2006.01)
*A61M 39/00* (2006.01)

(52) U.S. Cl.
CPC .... *A61M 5/14212* (2013.01); *A61M 5/14546* (2013.01); *A61M 39/22* (2013.01); *A61M 39/223* (2013.01); *A61M 39/24* (2013.01); *A61M 5/002* (2013.01); *A61M 5/14566* (2013.01); *A61M 39/26* (2013.01); *A61M 2039/009* (2013.01); *A61M 2039/0027* (2013.01); *A61M 2205/11* (2013.01); *A61M 2209/06* (2013.01)

(56) References Cited

U.S. PATENT DOCUMENTS

| | | | |
|---|---|---|---|
| 8,463,362 B2 * | 6/2013 | Fago | A61M 5/1413 600/420 |
| 2005/0234428 A1 * | 10/2005 | Spohn | A61M 5/007 604/533 |
| 2007/0179453 A1 * | 8/2007 | Lim | A61B 90/90 604/218 |
| 2008/0071219 A1 | 3/2008 | Rhinehart et al. | |

* cited by examiner

MULTI-DOSE DISPOSABLE SYSTEM

CROSS-REFERENCE TO RELATED APPLICATIONS

This application claims priority to U.S. Provisional Patent Application No. 61/941,153, filed Feb. 18, 2014, entitled "Multi-Dose Disposable System", which is hereby incorporated by reference in its entirety.

BACKGROUND

Field

This disclosure relates, in general, to the field of medical injectors, and, more particularly, to a multi-dose disposable system for use with a fluid injection system.

Description of the Related Art

In many medical diagnostic and therapeutic procedures, a medical practitioner, such as a physician, injects a patient with a fluid. In recent years, a number of injector-actuated syringes and powered injectors for pressurized injection of fluids have been developed for use in procedures, such as angiography, computed tomography, ultrasound, and NMR/MRI. In general, these powered injectors are designed to deliver a preset amount of fluid at a preset flow rate. The powered injectors are configured to deliver one or both of a contrast solution ("contrast") and a flushing solution, such as saline.

Presently, contrast and saline are provided in containers, such as sterilized glass bottles or flexible plastic bags. Because contrast and saline are injected into the patient, these fluids must be sterile and substantially void of contaminants. Additionally, a fluid path that delivers the contrast and saline from the container to the patient must be sterilized. Various medical connectors are known in the art for providing a fluid connection at various points between the containers and the patient. Conventional medical connectors and fluid path elements are generally provided in pre-sterilized, sealed packages prior to use. A user, such as a medical practitioner, must remove the medical connector from its package and connect it prior to use. While it is possible to maintain sterility in manufacturing and packaging of medical connectors, various sources of contamination may be introduced as soon as the medical connector is removed from the pre-sterilized, sealed package. For example, airborne particles, such as germs in droplets from coughs or sneezes, may accumulate on a fluid connection element of the medical connector, thereby contaminating it. Spores and dust are additional airborne particulates that may contaminate the medical connector. In use, the medical connector may be contaminated by inadvertent contact with a non-sterile material, such as the clothing or body of a medical practitioner or a patient. Sterility may be further compromised in the process of making a connection between a medical connector and a medical container by touching a non-sterile surface.

Even though various medical connectors of myriad designs have been used for many years, they are associated with a number of drawbacks. During use, it is essential that all contact with non-sterile surfaces is avoided and that exposure to airborne contaminants is reduced or minimized, or eliminated. Each time a fluid connection is established between a medical article, such as a syringe, a dosage container or a pump, and a fluid line connected to a patient, such as a catheter inserted into the patient, a new, sterile medical connector or fluid path element should be used to connect the fluid line between the medical article and the patient. However, sterility of connection between various medical connector components is often compromised if the connection is not made in a sterile environment, such as in a pharmacy or lab under a laminar flow hood. Most connections are not made in this manner. In a multi-patient system, a single non-sterile connection has the risk of compromising the sterility of the entire multi-patient system for multiple patients.

SUMMARY

In view of the difficulties in maintaining sterility of known multi-patient systems, there is a need for an improved multi-dose disposable system that overcomes the disadvantages of the existing systems. The multi-dose disposable system described hereinafter is configured to address these issues.

According to one aspect of the disclosure, a multi-dose fluid delivery system is disclosed. In one embodiment, the multi-dose fluid delivery system may include a multi-use fluid path set having a first end configured for fluidly connecting to at least one fluid source and a second end configured for fluidly connecting to a fluid injection apparatus. The multi-dose fluid delivery system may further include a plurality of single-use fluid path sets connected in sequence to define a fluid path extending from a first single-use fluid path set to a last single-use fluid path set. Each of the plurality of single-use fluid path sets may have a first end and a second end. The first end of the first single-use fluid path set may be configured for fluidly connecting to a patient delivery line. The second end of the last single-use fluid path set may be configured for fluidly connecting to the fluid injection apparatus. The second end of the first single-use fluid path set may be removable to expose the first end of a second or the last single-use fluid path set to which the patient delivery line is then connectable.

In accordance with another embodiment, the multi-dose fluid delivery system may further include a first fluid container having a first connection port and a second fluid container having a second connection port. A first fluid line may be configured for connecting the first connection port to a first syringe or first pressurizing or pumping apparatus of the fluid injection apparatus and a second fluid line may be configured for connecting the second connection port of the second fluid container to a second syringe or second pressurizing or pumping apparatus of the fluid injection apparatus. The multi-dose fluid delivery system may further include a delivery line configured for fluidly connecting the second end of the last single-use fluid path set with the fluid injection apparatus. A casing may be provided for receiving the multi-use fluid path set and the plurality of single-use fluid path sets. The casing may have a foldable structure that is foldable between a closed configuration and an open configuration. The system may include a manifold with an inlet for receiving fluid from the fluid injection apparatus and a plurality of outlets, each outlet in fluid connection with one single-use fluid path set. Each of the plurality of outlets has a valve switchable from a first position for fluid flow to a next valve and a second position for fluid flow to the single-use fluid path set connected to the valve. The manifold may be deconstructable in that a part of the manifold may be removed with one of or each of the single-use fluid path sets. A sealed member may be provided for enclosing the first connection port, the second connection port, and the first end of the multi-use fluid path set.

In accordance with another embodiment, a fluid injection system may include a fluid injector having an injector housing defining at least one syringe port for receiving at least one syringe, and a multi-dose fluid delivery system configured for fluidly connecting with the at least one syringe of the fluid injector. The multi-dose fluid delivery system may include at least one fluid container configured for receiving a medical fluid. The at least one fluid container may have a connection port, a multi-use fluid path set having a first end configured for fluidly connecting to the connection port of the at least one fluid container and a second end configured for fluidly connecting to the at least one syringe of the fluid injector, and a plurality of single-use fluid path sets connected in sequence to define a fluid path extending from a first single-use fluid path set to a last single-use fluid path set. Each of the plurality of single-use fluid path sets may have a first end and a second end. The first end of the first single-use fluid path set may be configured for fluidly connecting to a patient delivery line. The second end of the last single-use fluid path set may be configured for fluidly connecting to the at least one syringe of the fluid injector. The second end of the first single-use fluid path set may be removable to expose the first end of a second or the last single-use fluid path set to which the patient delivery line is then connectable. The at least one fluid container may be a first fluid container having a first fluid and a second fluid container having a second fluid.

In accordance with another embodiment, the fluid injection system may further include a first fluid line configured for connecting the connection port of the first fluid container to a first syringe of the fluid injector, a second fluid line configured for connecting the connection port of the second fluid container to a second syringe of the fluid injector, and a delivery line having a first end connected to the second end of the last single-use fluid path set and a second end configured for fluidly connecting to at least one of the first syringe and the second syringe of the fluid injector. A manifold may connect the first fluid line to the first syringe, the second fluid line to the second syringe, and the delivery line to at least one of the first syringe and the second syringe. The manifold may include at least one check valve. A sealed member may be provided for enclosing the connection port of the at least one fluid container and the first end of the multi-use fluid path set. The fluid path extending from the at least one fluid container to and through the single-use fluid paths may be a sterile fluid path whose sterility is maintained through the connection, filling, priming, and delivery phases of operation.

In accordance with another embodiment, a fluid path set assembly may include a plurality of separable single-use fluid path sets connected in sequence to define a fluid path extending from a first single-use fluid path set to a last single-use fluid path set. Each of the plurality of single-use fluid path sets may have a first end and a second end along a longitudinal length thereof. The first end of the first single-use fluid path set may be configured for fluidly connecting to a patient delivery line. The second end of the last single-use fluid path set may be configured for fluidly connecting to a fluid injector. The second end of each of the plurality of single-use fluid path sets may have a removable cap. The fluid path set assembly may further include a manifold having an inlet for receiving fluid from the fluid injector and a plurality of outlets. Each outlet may be in fluid connection with one single-use fluid path set. Each of the plurality of outlets may have an outlet valve movable from an initially-closed position to an open position. Each outlet valve may further be movable from the open position to a permanently-closed position. Each of the plurality of single-use fluid path sets may have a connector connected to the valve of a corresponding outlet. The second end of the first single-use fluid path set may be removable to expose a first end of a second single-use fluid path set to which the patient delivery line is then connectable.

These and other features and characteristics of the multi-dose fluid delivery system, the fluid injection system, and the fluid path set assembly, as well as the methods of operation and functions of the related elements of structures and the combination of parts and economies of manufacture, will become more apparent upon consideration of the following description and the appended claim with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and the claims, the singular form of "a", "an", and "the" include plural referents unless the context clearly dictates otherwise.

DETAILED DESCRIPTION

Figure 1:
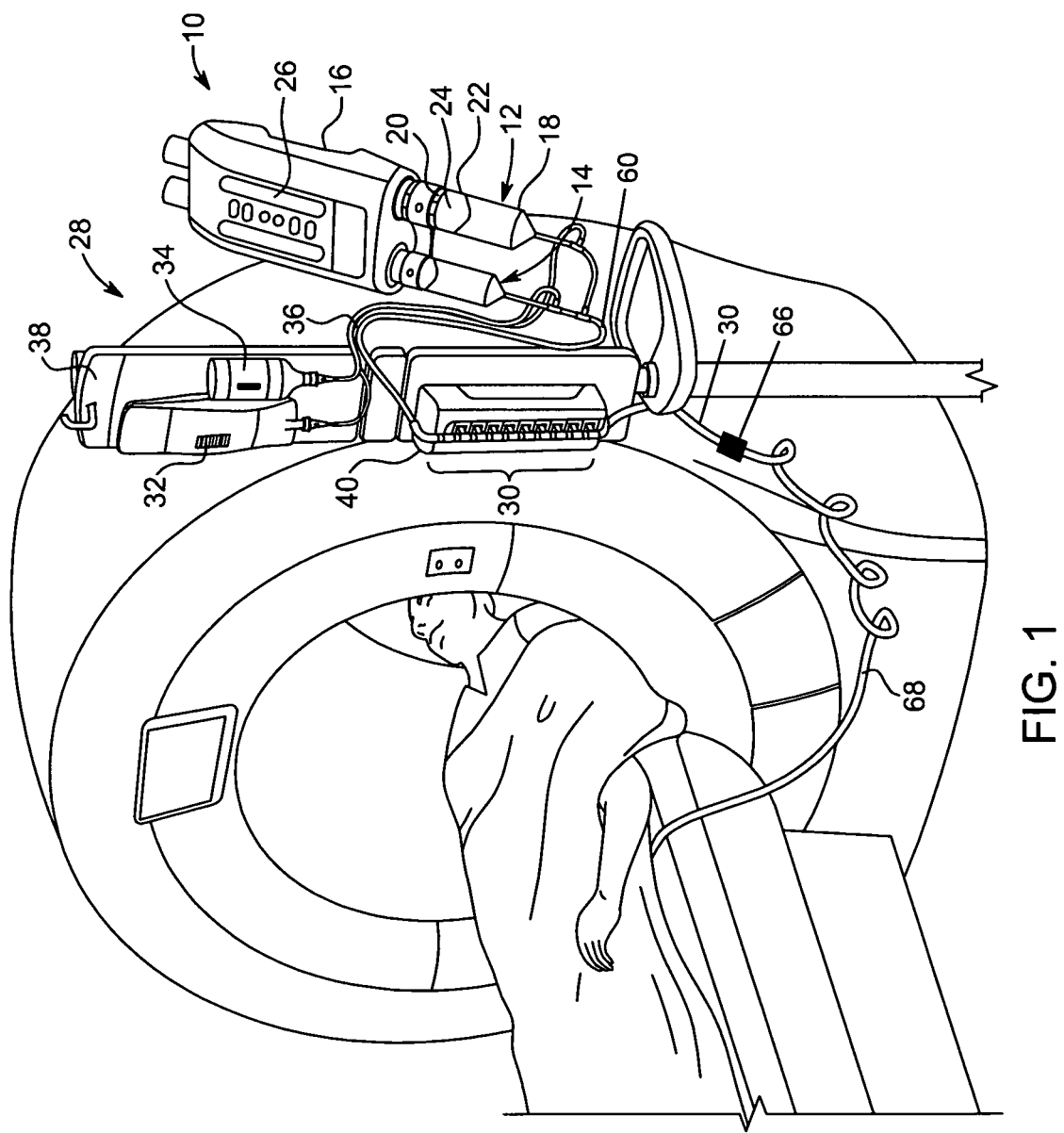
FIG. 1 is a perspective view of a multi-dose disposable system in use with a medical injector.

For purposes of the description hereinafter, spatial orientation terms, if used, shall relate to the referenced embodiment as it is oriented in the accompanying drawing figures or otherwise described in the following detailed description. Particularly, the term "proximal" refers to an end of a syringe nearer to an operator's hand or to a drive mechanism of a powered injector. The term "distal" refers to the end of a syringe farthest away from the operator's hand, where fluid is ejected from the syringe. However, it is to be understood that the embodiments described hereinafter may assume many alternative variations and embodiments. For example, other pumping means such as peristaltic pumps, piston pump, or multiple inline syringe (MILS) pump may be used. For example, one or more of the syringes could be replaced by the peristaltic pump module used by Swiss Medical which is now owned by Bracco Imaging SpA, of Italy. Alternatively, one or more of the syringes can be replaced by a tubing segment suitable for use in the pumps manufactured by Ulrich Gmbh of Ulm Germany. Alternatively, one or more of the syringes can be replaced by a bag to be used in the pump manufactured by Medex, a Guerbet Group company. It is also to be understood that the specific devices illustrated in the accompanying drawing figures and described herein are simply exemplary and should not be considered as limiting.

Referring to the drawings in which like reference characters refer to like parts throughout the several views thereof, a multi-dose disposable system for injecting one or more medical fluids to a patient is illustrated in detail.

With reference to FIG. 1, a powered medical fluid injector 10 is illustrated, which is adapted to interface with and actuate a plurality of syringes, which may be filled with contrast media, saline solution, or any desired medical fluids. For example, a first syringe, referred to hereinafter as a saline syringe 12, may be filled with the saline solution. A second syringe, referred to hereinafter as a contrast syringe 14, may be filled with the contrast media. The powered injector 10 may be used during a medical procedure to pressurized and inject contrast and saline into the body of a patient, either simultaneously or sequentially. The powered injector 10 is desirably at least a dual-syringe injector, wherein the two fluid delivery syringes are oriented in a side-by-side relationship and which are separately actuated by respective linear actuators or piston elements, associated with the powered injector 10.

The injector 10 may be enclosed within a housing 16 formed from a suitable structural material, such as medical grade plastic. The housing 16 may be in various shapes and sizes depending on the desired application. For example, the injector 10 may be a free-standing structure configured to be placed on the floor or may be a smaller design for placement on a suitable table or frame. The injector 10 includes syringe ports for connecting the saline syringe 12 and the contrast syringe 14 to respective piston elements. The syringe ports are located on a top side of the housing 16. The syringes 12, 14 generally have a cylindrical syringe barrel 18 formed from glass or medical-grade plastic. The barrel 18 has an open proximal end 20 and a nozzle 22 extending from its distal end. The open proximal end 20 may be sealed with an elastomeric plunger 24 that is slideable through the barrel 18. The plunger 24 forms a liquid tight seal against the sidewall of the barrel 18 as it is advanced therethrough. To preserve the sterility of the inside of the sidewall of the barrel 18, any of the means known to those skilled in the art may be used. For example, the barrel 18 may seal against the injector housing and the air that moves in and out of the barrel 18 as the piston and plunger are moved can be sterile air created by a sterile filter. Alternatively, a flexible mechanical seal such as a baggie, condom, or flexible bladder similar to that use on the pump piston of systems manufactured by Possis Medical, Inc. of Minneapolis, Minn. may be used.

The injector 10 has a control panel 26 for controlling the operation of the injector 10. For example, the control panel 26 may have one or more input devices, such as buttons, levers, dials, or touch screens, to set the desired injection parameters. The flow of saline solution from the saline syringe 12 and contrast from the contrast syringe 14 may be regulated at the control panel 26 which controls various valves and flow regulating structures to regulate the delivery of the saline solution and contrast to the patient based on user selected injection parameters, such as injection flow rate, pressure, duration, total injection volume, and ratio of contrast media and saline. A suitable multi-syringe injector 10 is described in U.S. patent application Ser. No. 13/386,765, filed on Jan. 24, 2012, published as U.S. Patent Application Publication No. 2012/0123257, and assigned to the assignee of the present application, the disclosure of which is incorporated herein by reference in its entirety. Other relevant multi-fluid delivery systems are found in U.S. patent application Ser. No. 10/159,592, filed on May 30, 2002 (published as U.S. 2004/0064041) and in U.S. patent application Ser. No. 10/722,370, filed Nov. 25, 2003 (published as U.S. 2005/0113754), assigned to the assignee of the present application, and the disclosures of which are both incorporated herein by reference.

A multi-dose disposable system 28 (hereinafter referred to as "system 28") is configured for connection with the injector 10 for delivering fluid to and from the syringes 12, 14 to a patient via a patient delivery line 68 at a vascular access site via a single-use fluid path set 30. The patient delivery line may be, for example, a vascular access site, an IV in a vein, a PICC line or other central catheter, a port, an arterial catheter, or any other medical device used to deliver fluid to a patient. The patient delivery line 68 may be as short as the hub of a catheter in the arms of the patient or of whatever length is advantageous for the healthcare worker. The system 28 includes a source of saline, such as a saline container 32, and a source of contrast, such as a contrast container 34. The system may include a third or more fluids, for example, a cardiac stress agent for cardiac imaging studies. It may also contain more than one type of contrast or other active fluids. The containers 32, 34 may be embodied as glass containers or flexible plastic bags, as is known in the art. The system 28 further includes a multi-use fluid path set 36 for connecting the containers 32, 34 with the syringes 12, 14, respectively. Additionally, the system 28 includes a plurality of single-use fluid path sets 30 for connecting with the output fluid path element of the injector, in this embodiment the delivery line 60 coming from syringes 12, 14.

Figure 2:
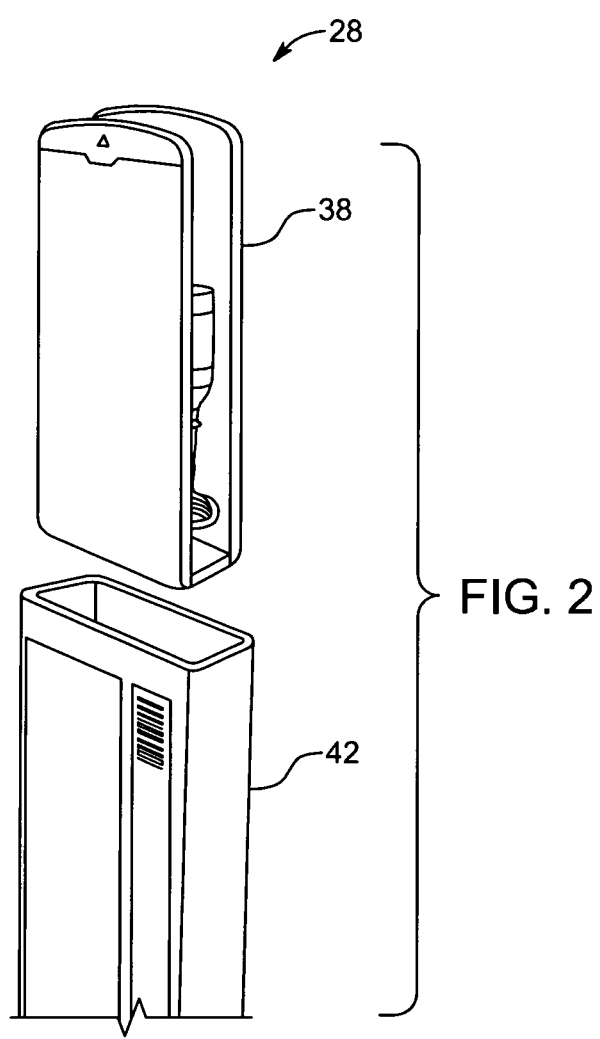
FIG. 2 is a perspective view of the multi-dose disposable system and its associated packaging.

The containers 32, 34, the multi-use fluid path set 36, and the plurality of single-use fluid path sets 30 are contained within a casing 38. As shown in FIG. 1, the casing 38 may be embodied as a foldable substrate that supports the containers 32, 34 on one end and a receiver 40 for the plurality of single-use patient fluid sets 30 on the opposite end. In a first configuration, shown in FIG. 2, the casing 38 is folded for easier portability and to protect the contents thereof during transport. In a second configuration, shown in FIG. 1, the casing 38 is unfolded or opened to allow the user to access the contents thereof and make the appropriate syringe and fluid connections to the injector 10 and the patient. The casing 38 may be packaged within a shipping package 42 (shown in FIG. 2) to prevent damage during transport.

Figure 3:
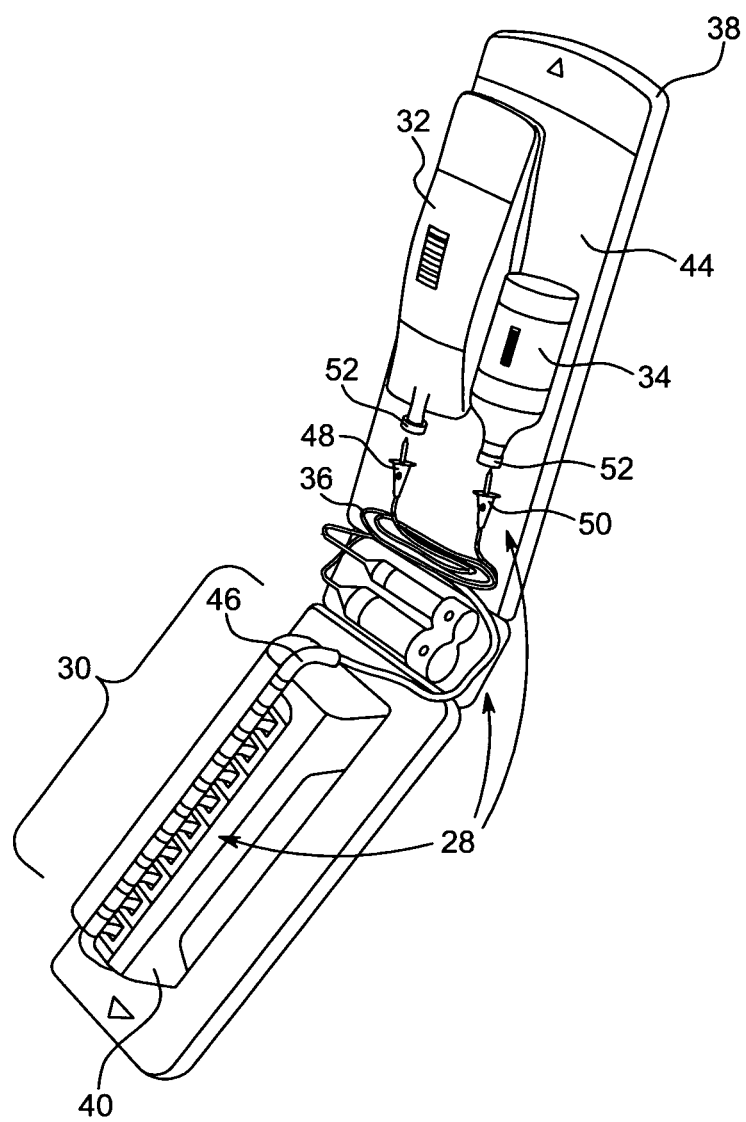
FIG. 3 is a perspective view of the multi-dose disposable system in accordance with one embodiment.

With reference to FIG. 3, the system 28 is shown in an open state and removed from the shipping package 42. Initially, such as during shipment and prior to initial use, the containers 32, 34 are not connected to the multi-use fluid path set 36. Rather, the multi-use fluid path set 36 may be disposed in a sealed, sterilized bag or bellows 44 that preferably encloses at least the necks or septums of containers 32, 34 and at least a portion of the multi-use fluid path set 36. The bag 44 may be sealed around a perimeter of the casing 38 during manufacture, where it can be assured that the components within the bag 44 are sterile and that no contaminants are introduced into the bag 44. For example, a clean, but not sterile, multi-use fluid path set 36 may be placed near the containers 32, 34 but not in fluid connection with the containers 32, 34. The bag 44 is then sealed relative to the casing 38 such that the containers 32, 34 and the multi-use fluid path set 36 are within a sealed space defined between the bag 44 and the casing 38. The entire assembly, including the receiver 40 and the plurality of single-use fluid path sets 30 may then be sterilized using a known sterilization method, such as gas sterilization or gamma or e-beam irradiation. For a gas sterilization method to work, the sealed space within the bag 44 must at least partially open or permeable to allow for the gas to be introduced into the sealed space. With gamma and/or e-beam irradiation, it is desirable to expose the connection between the containers 32, 34 and the multi-use fluid path set 36 while preventing or reducing the exposure of the bulk fluid. The fluid inside the containers 32, 34 tends to be denser than the plastic of the multi-use fluid path set 36, which causes it to absorb a significant amount of the radiation, thereby requiring either longer irradiation times or higher dose rates. In addition, the radiation can negatively impact the fluid or the packing in contact with the fluid.

In another embodiment, the multi-use fluid path set 36 is packaged in a separate, sterile package (not shown), or it may be provided separately from the system 28. In this embodiment, the connection between the multi-use fluid path set 36 and the containers 32, 34 may be established under sufficiently sterile conditions, such as under a laminar air hood or using sterile technique in the imaging suite.

With continuing reference to FIG. 3, the receiver 40 holds a plurality of single-use fluid path sets 30. The plurality of single-use fluid path sets 30 is connected together to define a sterile fluid path 46. The ends of each single-use fluid path sets 30 have caps (either vented or unvented) that preserve the sterility of the sterile fluid path 46. The outside of the sterile fluid path 46 may be open to the air and not sterile.

Figure 4:
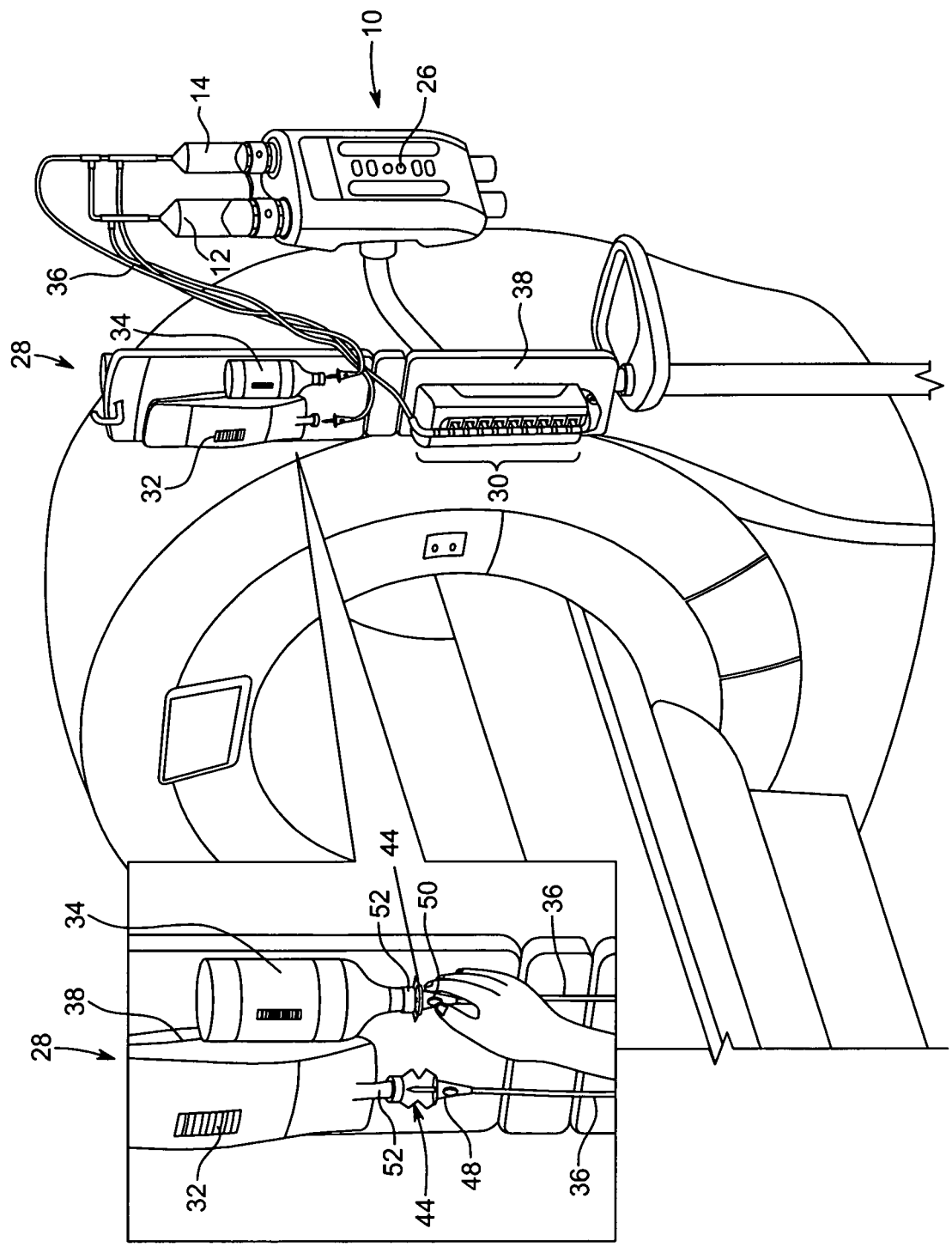
FIG. 4 is a perspective view of the multi-dose disposable system being connected to the medical injector.

Fluid connection between the containers 32, 34 and the multi-use fluid path set 36 is established by connecting a saline spike 48 to the saline container 32 and connecting a contrast spike 50 to the contrast container 34, as shown in FIG. 4. This connection can be accomplished in several ways. In the embodiment where the multi-dose fluid path set 36 is sealed within the bag 44, the connection is made by simply inserting the spikes 48, 50 into fluid ports 52 of the corresponding containers 32, 34. The bag 44 desirably provides sufficient space for the user to manipulate the spikes 48, 50 for connection with the fluid ports 52 within the sealed space of the bag 44. In the embodiment where the multi-use fluid path set 36 is not provided within the sealed bag 44, the connection may be made under a laminar air hood or other suitable environment by inserting the spikes 48, 50 into fluid ports 52 of the corresponding containers 32, 34.

Figure 5:
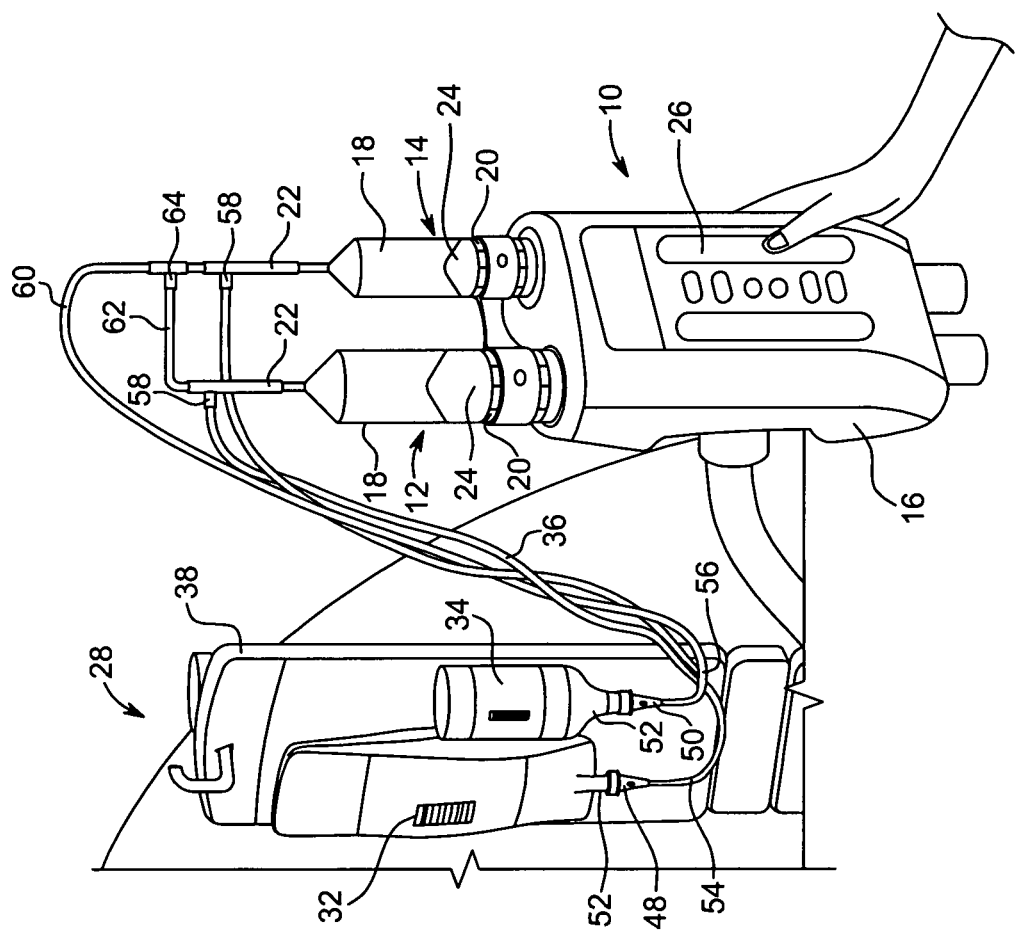
FIG. 5 is a perspective view of the multi-dose disposable system filling a syringe of the medical injector.

Once the spikes 48, 50 are connected with the fluid ports 52 of the corresponding containers 32, 34, the multi-use fluid path set 36 is connected to the injector 10. With reference to FIG. 5, the multi-use fluid path set 36 includes a saline fluid line 54 configured for connecting to the nozzle 22 of the saline syringe 12 and a contrast fluid line 56 configured for connecting to the nozzle 22 of the contrast syringe 14. Two-way check valves 58 may be provided at the connection between the saline and contrast lines 54, 56 with the saline and contrast syringes 12, 14. The outlet of the nozzles 22 of the saline and contrast syringes 12, 14 is connected to a delivery line 60 by way of a manifold 62. The manifold 62 may have one or more check valves 64 to prevent the fluid delivered from the syringes 12, 14 from flowing back into the syringes 12, 14 or into the multi-use path 36 or fluid containers 32, 34. The delivery line 60 is connected to the remainder of the sterile fluid path 46 (shown in FIG. 6) for delivering the fluid from the syringes 12, 14 to the plurality of single-use fluid path sets 30, as will be described with reference to FIG. 6. The fluid from the containers 32, 34 is aspirated into the syringes 12, 14 by selectively activating the plungers 24 to move from a distal end adjacent to the nozzle 22 in a proximal direction of the barrel 18. Using the control panel 26, the user may define the volume of saline and contrast that is aspirated into the saline and contrast syringes 12, 14. During aspiration, the injector 10 is desirably oriented in an upward orientation such that the nozzles 22 of the syringes 12, 14 point upwards to facilitate the removal of air from the syringes.

Figure 6:
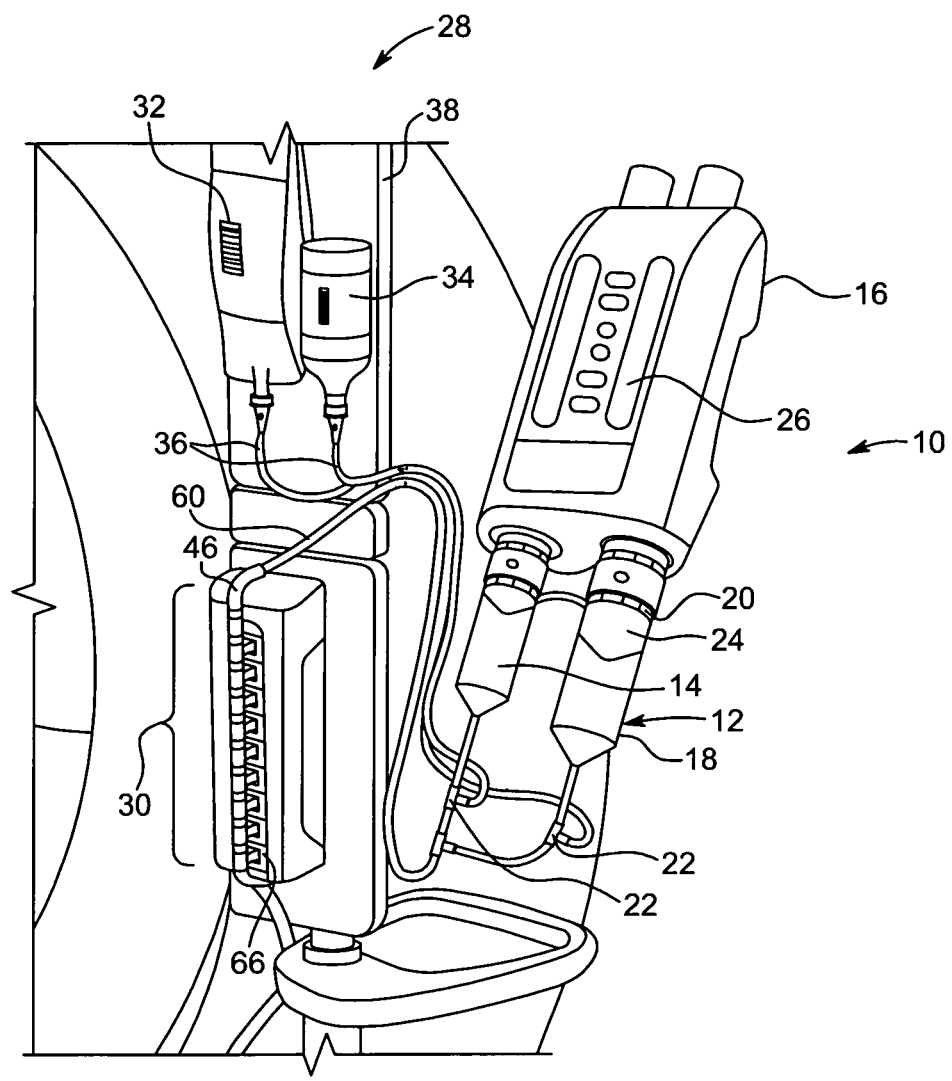
FIG. 6 is a perspective view of the multi-dose disposable system and the medical injector in a state prior to being connected to a patient.

With reference to FIG. 6, once the saline and contrast are aspirated into the syringes 12, 14, the system 28 can be primed before being connected to a patient for delivering the fluids to the patient. The fluid is dispensed from the syringes 12, 14 by selectively activating the plungers 24 to move from the proximal end adjacent to the housing 16 in a distal direction of the barrel 18. Using the control panel 26, the user may define the volume and flow rate of saline and contrast that is delivered from the saline and contrast syringes 12, 14. During this pump priming step, any air that is present in the syringes 12, 14 and some fluid is delivered from the syringes 12, 14 into the delivery line 60. In some embodiments, the air and/or fluid could optionally be delivered to a waste container (not shown) provided between the tip of syringes 12, 14 and the receiver 40. In other embodiments, the fluid can remain in the delivery line 60. In other embodiments, the bottom-most position on receiver 40 may be a waste bag to receive the expelled air and fluid. Once all air is removed from the syringes 12, 14 in preparation for delivery, the injector 10 is desirably oriented in a downward orientation such that the nozzles 22 of the syringes 12, 14 point downwards so that any air that may be drawn into the syringe(s) 12, 14 during filling or refilling will not be conveyed through the delivery line 60 towards the patient. Alternatively, air sensors or detectors, as known in the art may, be incorporated to alert the user and as appropriate stop system operation if air is detected. Following this practice, only contrast, saline, or a mixture thereof from the delivery line 60 may be delivered to the sterile fluid path 46. The sterile fluid path 46 is defined by the plurality of single-use fluid path sets 30 which are connected together in a serial or sequential arrangement by a plurality of connectors 66. The connectors 66 have valves that allow the fluid to flow to the next connector 66 or to a patient line 68 (shown in FIG. 7D). In some embodiments, the connection between the plurality of single-use fluid path sets 30 may be a series connection, where fluid may be delivered from a first single-use fluid path set 30 to a last single-use fluid path set 30 in one, continuous fluid path that extends through each of the single-use fluid path sets 30. In other embodiments, the connection between the plurality of single-use fluid path sets 30 may be a sequential connection, where fluid may be delivered to a manifold having a plurality of valves, with each valve configured for removable connection with a corresponding single-use fluid path set 30.

Figure 7A:
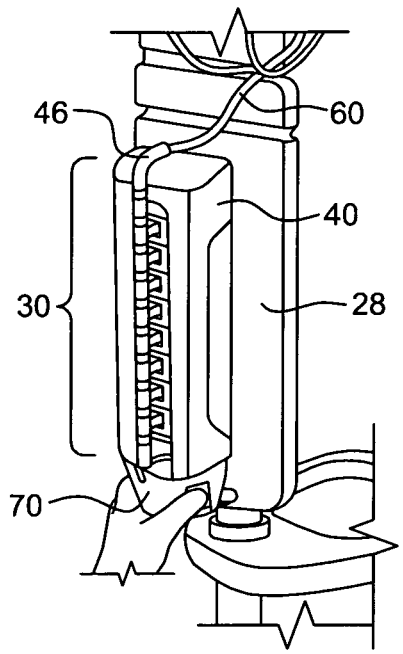
FIGS. 7A-7D are various perspective views of the multi-dose disposable system being prepared for delivering fluid to a first patient.
Figure 7B:
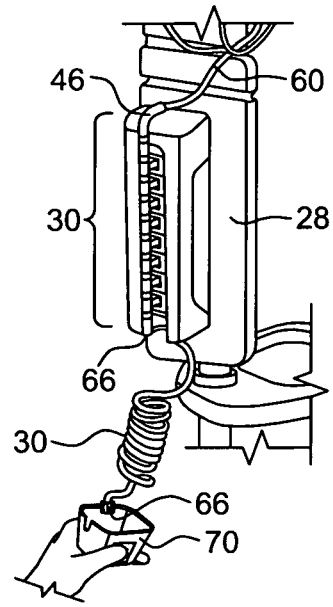
Figure 7C:
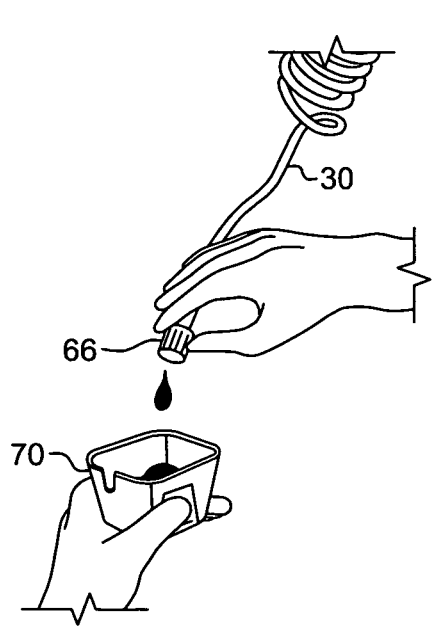
Figure 7D:
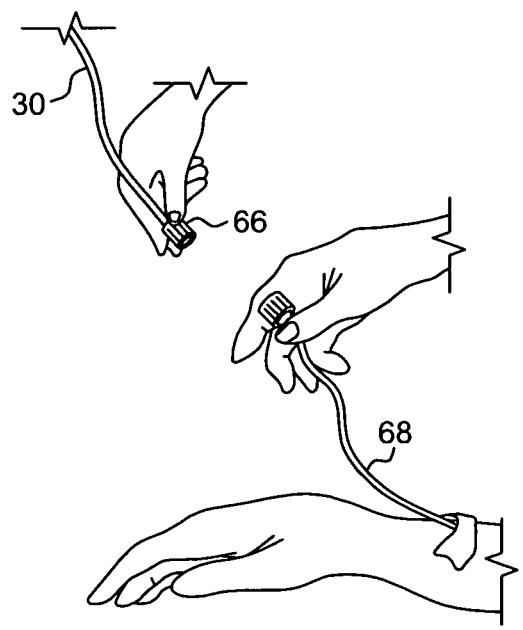

Referring to FIGS. 7A-7D, the process of using the single-use fluid path set 30 will be described. As shown in FIGS. 7A-7B, the user removes a protective lid 70 to expose the single-use fluid path set 30 and its corresponding connector 66. Each single-use fluid path set 30 has a fluid path with a single connector 66 disposed at each end thereof. Once exposed, the single-use fluid path set 30 is primed (i.e., filled with fluid). The protective lid 70 may be configured for collecting any extra fluid that may drip from the connector 66 (as shown in FIG. 7C) before the connector 66 is connected to the patient line 68 in a manner known in the art (FIG. 7D). Once connected to the patient line 68, the fluid from the syringes 12, 14 may be delivered to the patient by activating the injector 10 to deliver the fluid to the single-use fluid path set 30 by way of the multi-use fluid path set 36.

Figure 8A:
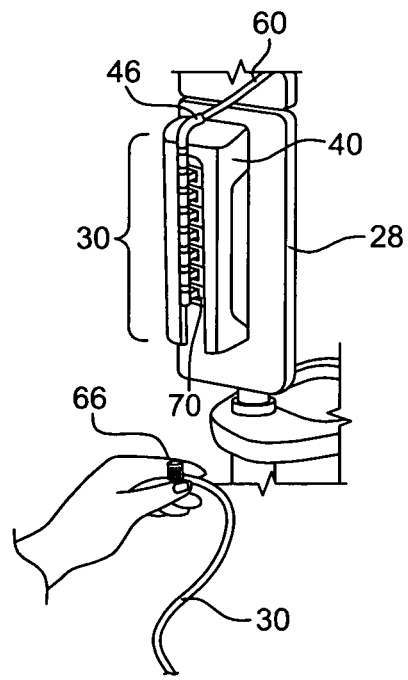
FIGS. 8A-8C are various perspective views of the multi-dose disposable system being prepared for delivering fluid to a subsequent patient.
Figure 8B:
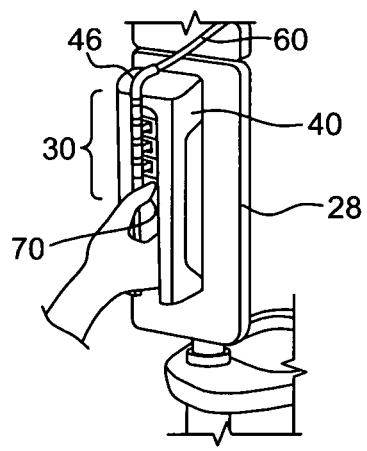
Figure 8C:
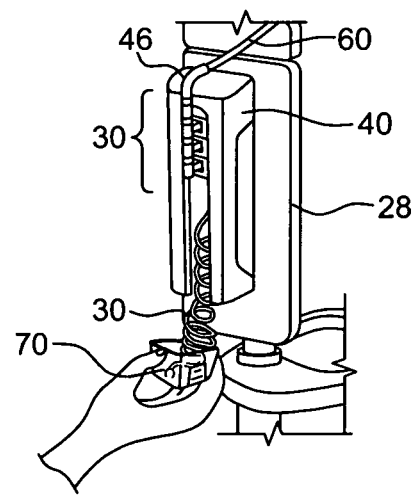

With reference to FIGS. 8A-8C, the process of disposing of a used single-use fluid path set 30 and preparing a subsequent single-use fluid path set 30 for use will be described. Referring initially to FIG. 8A, the used single-use fluid path set 30 is disconnected from an adjoining single-use fluid path set 30 by disconnecting the connector 66 from the sterile fluid path 46. Once disconnected, the protective lid 70 of the adjacent single-use fluid path set 30 is removed to expose next single-use fluid path set 30 and its connector 66. The next single-use fluid path set 30 can be primed and connected to the patient line 68 as described with reference to FIGS. 7C-7D. Once the last of the plurality of single-use fluid path sets 30 is utilized, or after the fluid from one or both of the containers 32, 34 is used, the multi-use fluid path set 36 is disconnected from the injector 10 and the entire system 28 is disposed of.

Figure 9A:
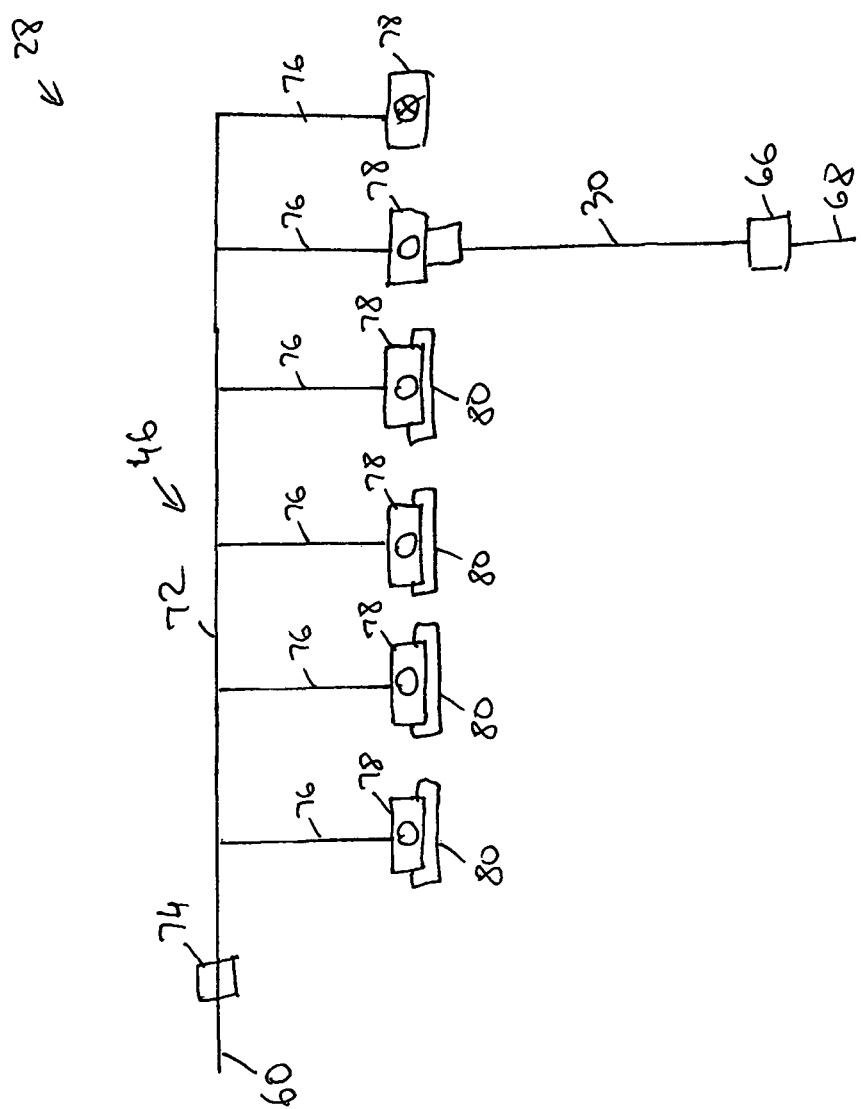
FIG. 9A is a schematic representation of the multi-dose disposable system in accordance with a second embodiment.

With reference to FIG. 9A, the system 28 is illustrated in accordance with a second embodiment. In this embodiment, the sterile fluid path 46 is formed as a manifold 72 having an inlet 74 that is configured for connection with the delivery line 60 of the multi-use fluid path set 36. The manifold 72 includes a plurality of outlets 76, with each outlet 76 having a single outlet valve 78. Each outlet valve 78 has a protective cap 80 that maintains the sterility of the outlet valve 78 prior to use. In one embodiment, the outlet valve 78 is a stopcock or valve that is configured to be moved in one direction only from an initially closed position to an open position and then to a permanently completely closed position, such as by a ratcheting movement. Each outlet valve 78 is connectable to the single-use fluid path set 30 by coupling one of the connectors 66 of the single-use fluid path set 30 with the outlet valve 78 after removing the protective cap 80. After the fluid delivery procedure is completed, the single-fluid path set 30 can be disconnected and the outlet valve 78 moved from the open position to the closed position. Due to the one-way action of the outlet valve 78, subsequent opening of the outlet valve 78 is prevented. A second single-use fluid path set 30 can be connected to the next unused outlet valve 78 in a similar manner. Once all of the outlet valves 78 have been used, the entire system 28 can be disposed of. In another embodiment, a plurality of single-use fluid path sets 30 may be pre-connected to the outlet valves 78. In FIG. 9A, only the second connector 66 of the single-use fluid path set 30 is shown connected to the patient line 68. In this embodiment, after a single use fluid path set 30 is used, the valve 78 is rotated to release the single use fluid path set 30 for removal. In doing so, that valve 78 is locked into the closed position.

Figure 9B:
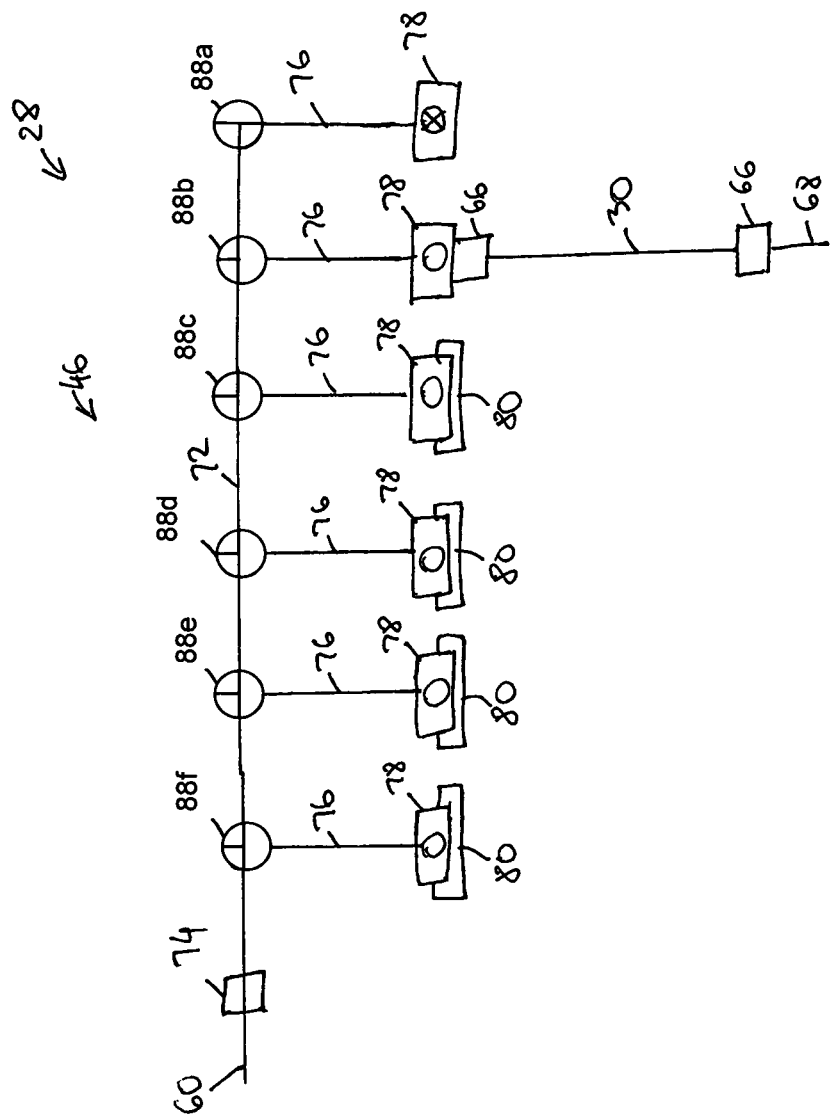
FIG. 9B is a schematic representation of another variation of the multi-dose disposable system shown in FIG. 9A.
Figure 9C:
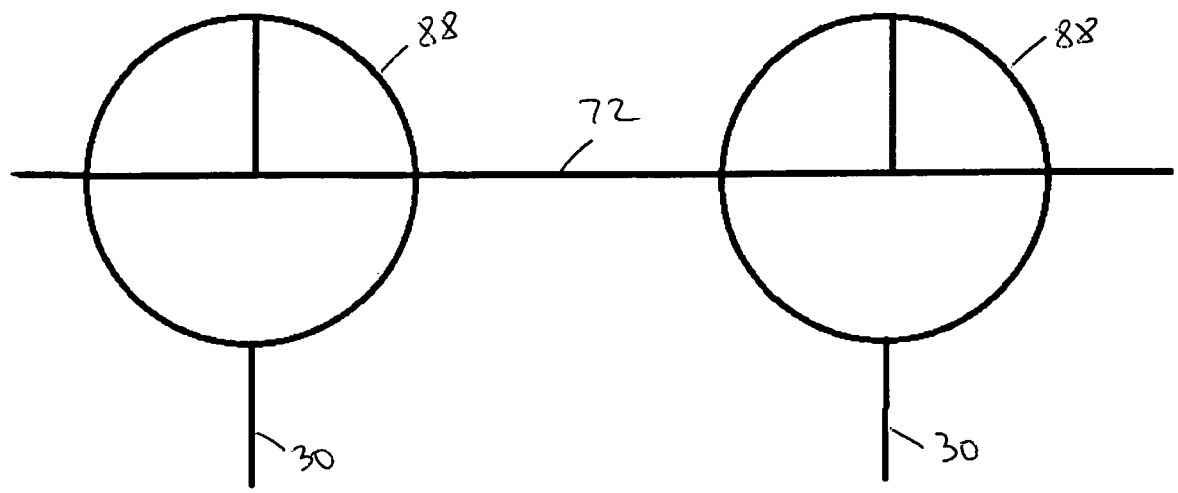
FIG. 9C shows a first position of a valve for delivering fluid downstream to a next valve.
Figure 9D:
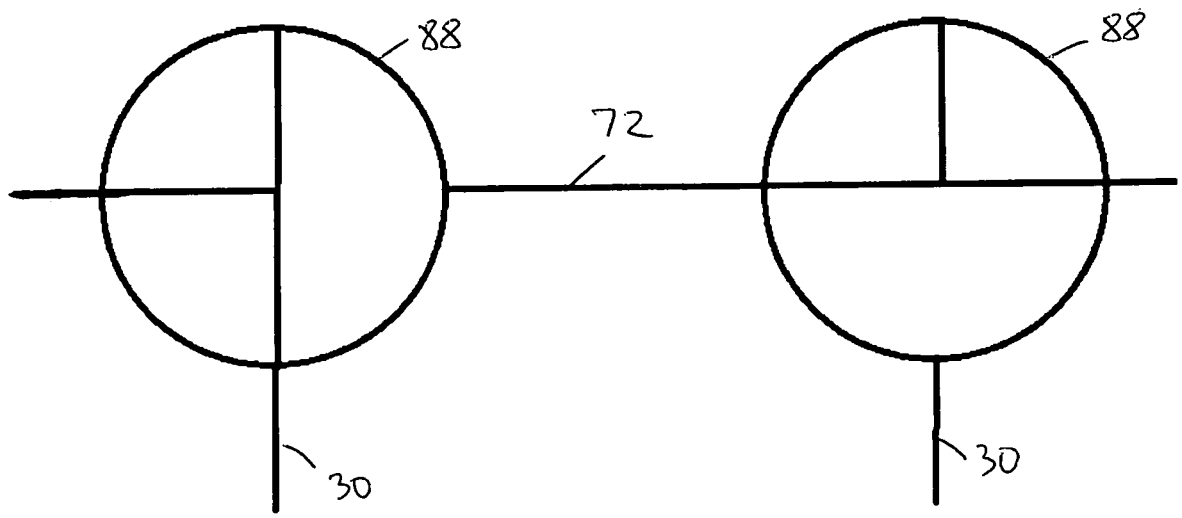
FIG. 9D shows a second position of the valve for delivering fluid to a single use fluid path set.

FIG. 9B shows another embodiment in which the valves 88a-88f are ratcheting stopcocks as described above in connection with FIG. 9A and the outlet valves 78' serve as connectors with protective caps 80. The valves 88a-88f are initially arranged to deliver fluid through a manifold 72. Fluid is initially delivered to a last valve 88a. After the single-use-fluid path set 30 that is connected to the valve 88a is used, valve 88b is irreversibly rotated, for example by 90 degrees (counterclockwise in the embodiment illustrated in FIG. 9B), to allow the subsequent fluid path set 30 to be connected to the valve 88b. The downstream fluid path elements may be removed. After that next single-use fluid path set 30 is used, valve 88c is irreversibly rotated, for example by 90 degrees, to allow the subsequent fluid path set 30 to be connected to the valve 88c. This sequence of events may be continued until all the fluid paths are used or insufficient fluid remains for another patient. FIG. 9C shows the position of the valve 88 to conduct the fluid downstream to the next valve and FIG. 9D shows the position of the valve 88 to conduct the fluid out the single use fluid path set 30.

Figure 10A:
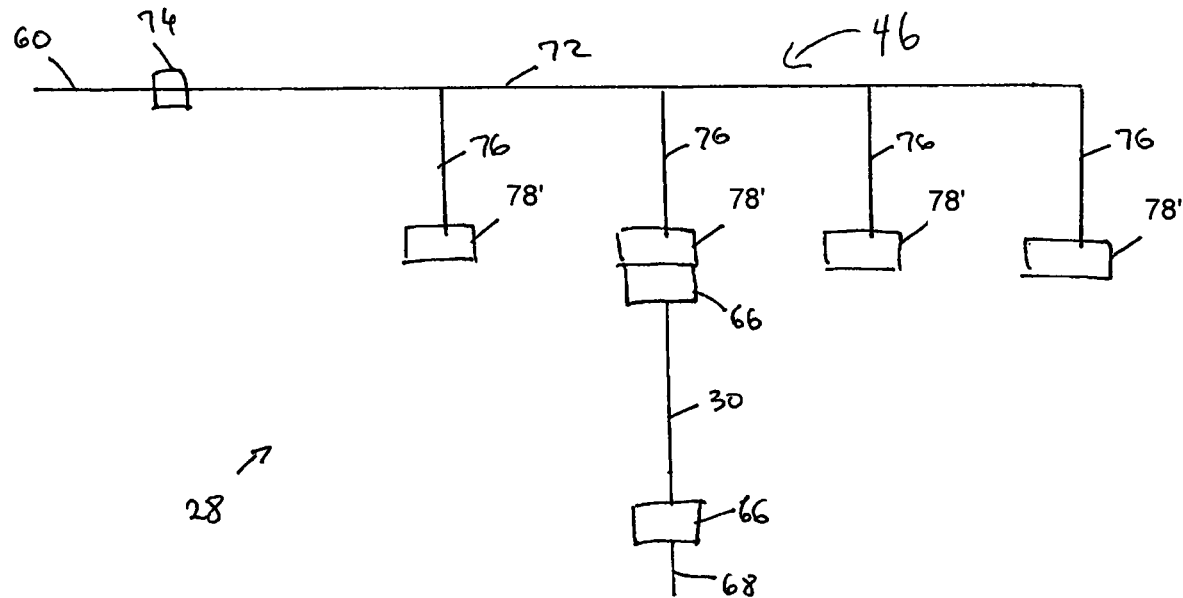
FIGS. 10A-10B are a schematic representation of the multi-dose disposable system in accordance with a third embodiment.
Figure 10B:
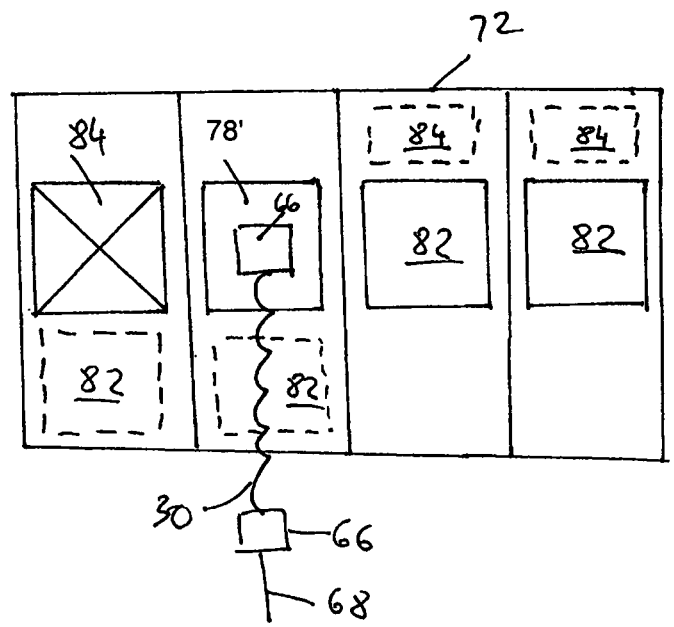

With reference to FIGS. 10A-10B, the system 28 is illustrated in accordance with a third embodiment. Similar to the embodiment described above with reference to FIG. 9A, the sterile fluid path 46 in this embodiment is formed as a manifold 72 having an inlet 74 that is configured for connection with the delivery line 60 of the multi-use fluid path set 36. The manifold 72 includes a plurality of outlets 76, with each outlet 76 having a single outlet valve 78'. Each outlet valve 78' has a first cover 82 that maintains the sterility of the outlet valve 78' prior to use. Each outlet valve 78' is connectable to one single-use fluid path set 30 by coupling its corresponding connector 66 with the outlet valve 78'. Before the connector 66 of the single-use fluid path set 30 can be connected with the outlet valve 78', the first cover 82 is urged by a sliding or rotating movement of the connector 66 from a first position, where the outlet valve 78' is protected, to a second position, where the outlet valve 78' is exposed and ready for connection with the connector 66. After the fluid delivery procedure is completed, the single-fluid path set 30 can be disconnected only by moving a second cover 84 that blocks the outlet valve 78'. Once the second cover 84 blocks the outlet valve 78', reuse of the outlet valve 78' is prevented. A second single-use fluid path set 30 can be connected to the next unused outlet valve 78' in a similar manner. Once all of the outlet valves 78' have been used, the entire system 28 can be disposed of.

Figure 11A:
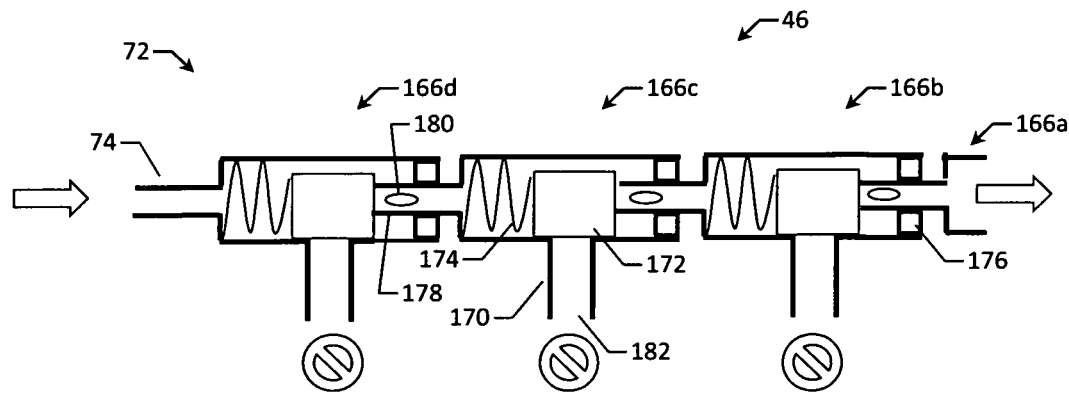
FIGS. 11A-11C are a schematic representation of the multi-dose disposable system in accordance with a fourth embodiment.
Figure 11B:
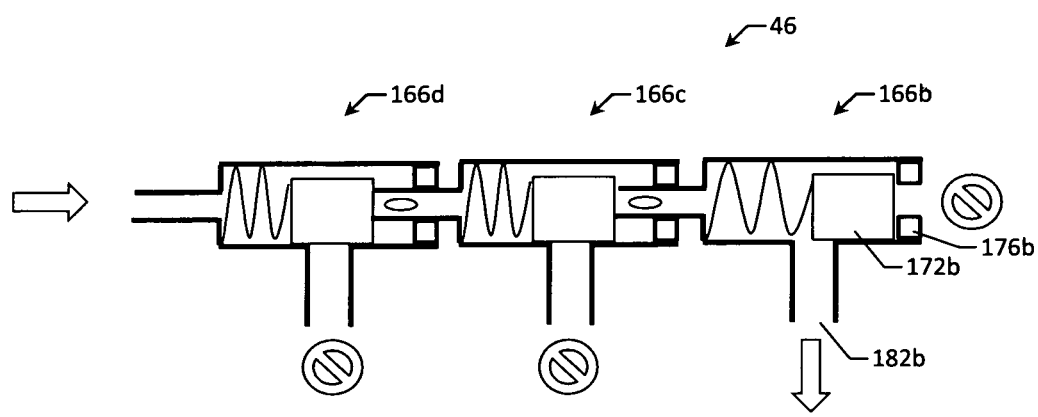
Figure 11C:
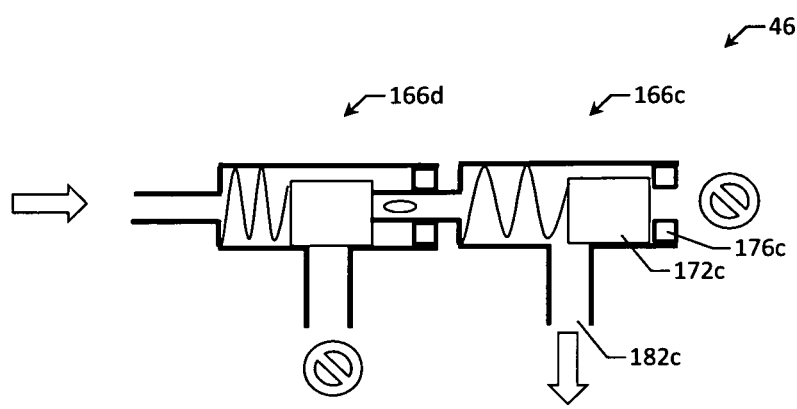

FIGS. 11A-11C show another embodiment where a segment of the sterile fluid path 46 in this embodiment is formed as a manifold 72 having an inlet 74 and one or more stackable spool valves, for example valves 166b, 166c, and 166d. Each spool valve 166b-166d has a housing 170 which defines an internal fluid path. Located inside the internal fluid path is a slider 172 and a resilient member 174, such as a compressible spring, that biases the slider 172 towards a seal 176. When an inlet 178 of a downstream valve 166 is inserted and secured in the opening surrounding the seal 176 by threads, latches, friction or other mechanism, the slider 172 is urged away from the seal 176 and a side port 182 is sealed off by the slider 172 so fluid coming in the inlet 178 flows around the slider 172, through an opening 180 on the inlet 178 and into the inlet 178 of the downstream valve 166 or other fluid path element, for example a single use fluid path set 30 (shown in FIGS. 10A-10B). The slider 172 is offset by ribs of other features in the housing 170 or the slider 172 toward a sidewall of the valve 166b-166d such that side port 182 is sealed off and a radial space is formed between the slider 172 and the opposing sidewall of the valve 166b-166d. Depending on the position of the slider 172 within the housing 170, fluid may flow through this radial space. When a procedure using most downstream single use fluid path set 30 is completed, the most downstream manifold element, for example valve 166a in FIG. 11A, is removed. The configuration of the fluid path 46 then becomes that of FIG. 11B. Slider 172b is free to move against seal 176b and in the process of moving, side port 182b is opened so that fluid can flow out to the attached single use tube, not shown. Similarly, when the procedure using that single-use tube is completed, valve 166b is removed. Slider 172c now moves against seal 176c closing off the end opening or port and side port 182c is now open to receive fluid for transmission to the patient. This process continues until one of the fluids is used up or all of the connectors are used. Thus the manifold may be considered to be being taken apart or deconstructed as individual valves 166a through 166c are removed between each patient after the single-use tube 30 is finished being used. The valves may be distinct from the second end of the single use fluid paths 30 or they may be incorporated as part of the second end of single-use fluid paths 30.

The various embodiments of the multi-dose disposable system 28 have been described to highlight the various benefits of the system 28. In one embodiment, the system 28 combines an injector 10 and a multi-use fluid path set 36 with a plurality of single-use fluid path sets 30. In this manner, the only connection that is made after the system 28 is connected to the injector 10 is the connection between the single-use fluid path set 30 and the patient line 68. The system 28 reduces fluid waste by optimizing the amount of fluid on a per patient basis for each single-use fluid path set 30. Alternatively, other embodiments describe variations and additional variations are possible where less than the full fluid path comes preassembled and sterilized. For example, an embodiment can utilize a number of preconnected patient tubes as in FIG. 9A and one or more of the connectors as in FIG. 10A which can have patient tubes added to them. Operators are sensitive to throwing away both unused contrast and patient tubes. One approach, depending upon the relative cost of contrast and tubes, is to always have a little extra of the least expensive aspect. An alternative is to have one or two connectors with no patient tubes attached. This allows the user to connect singly packaged patient tubes if just one or two more doses remain in the fluid container or syringes. If connectors without patient tubes are utilized, an alternative embodiment could use the sterility retaining medical connector assembly described in WO 2013059563 A1, which is incorporated herein by reference.

Several options have been discussed in regards to sterilization. Another aspect to be discussed is the option of either enclosing the sterile elements in a sterility preserving bag or wrap, or to cap the ends of the fluid path so that the inside and the relevant parts of the connectors remain sterile. This has the benefit of allowing more flexible packaging and positioning for installation and operation.

While several embodiments of the multi-dose disposable system are shown in the accompanying figures and described hereinabove in detail, other embodiments will be apparent to, and readily made by, those skilled in the art without departing from the scope and spirit of the disclosure. For example, it is to be understood that this disclosure contemplates that, to the extent possible, one or more features of any embodiment can be combined with one or more features of any other embodiment. Accordingly, the foregoing description is intended to be illustrative rather than restrictive.

What is claimed is:

1. A multi-dose fluid delivery system comprising:
   a multi-use fluid path set having a first end configured for fluidly connecting to at least one fluid source and a second end configured for fluidly connecting to a fluid injection apparatus; and
   a plurality of single-use fluid path sets connected in a series to define a fluid path extending from a first single-use fluid path set to a last single-use fluid path set, each of the plurality of single-use fluid path sets having a first end and a second end,
   wherein the first end of each single-use fluid path set is configured for fluidly connecting to the patient delivery line when any of the plurality of single-use fluid path sets is the first single-use fluid path set in the series of single-use fluid path sets,
   wherein the second end of the last single-use fluid path set is configured for fluidly connecting to the fluid injection apparatus; and
   wherein the second end of the first single-use fluid path set is removable from the series of the plurality of single-use fluid path sets to expose the first end of a next single-use fluid path set to which the patient delivery line is then connectable.

2. The multi-dose fluid delivery system of claim 1, wherein the at least one fluid source comprises a first fluid container having a first connection port and a second fluid container having a second connection port.

3. The multi-dose fluid delivery system of claim 2, further comprising a first fluid line configured for connecting the first connection port to a first syringe of the fluid injection apparatus and a second fluid line configured for connecting the second connection port of the second fluid container to a second syringe of the fluid injection apparatus.

4. The multi-dose fluid delivery system of claim 1, further comprising a delivery line configured for fluidly connecting the second end of the last single-use fluid path set with the fluid injection apparatus.

5. The multi-dose fluid delivery system of claim 2, further comprising a sealed member for enclosing the first connection port, the second connection port, and the first end of the multi-use fluid path set.

6. A fluid injection system comprising:
   a fluid injector having an injector housing defining at least one syringe port for receiving at least one syringe; and
   a multi-dose fluid delivery system configured for fluidly connecting with the at least one syringe of the fluid injector, the multi-dose fluid delivery system comprising:
   at least one fluid container configured for holding a medical fluid, the at least one fluid container having a connection port;
   a multi-use fluid path set having a first end configured for fluidly connecting to the connection port of the at least one fluid container and a second end configured for fluidly connecting to the at least one syringe of the fluid injector; and
   a plurality of single-use fluid path sets connected in a series to define a fluid path extending from a first single-use fluid path set to a last single-use fluid path set, each of the plurality of single-use fluid path sets having a first end and a second end,
   wherein the first end of each single-use fluid path set is configured for fluidly connecting to the patient delivery line when any of the plurality of single-use fluid path sets is the first single-use fluid path set in the series of single-use fluid path sets, wherein the second end of the last single-use fluid path set is configured for fluidly connecting to the at least one syringe of the fluid injector, and wherein the second end of the first single-use fluid path set is removable from the series of the plurality of single-use fluid path sets to expose the first end of a next single-use fluid path set to which the patient delivery line is then connectable.

7. The fluid injection system of claim 6, wherein the at least one fluid container is a first fluid container having a first fluid and a second fluid container having a second fluid.

8. The fluid injection system of claim 7, further comprising:
a first fluid line configured for connecting the connection port of the first fluid container to a first syringe of the fluid injector;
a second fluid line configured for connecting the connection port of the second fluid container to a second syringe of the fluid injector; and
a delivery line having a first end connected to the second end of the last single-use fluid path set and a second end configured for fluidly connecting to at least one of the first syringe and the second syringe of the fluid injector.

9. The fluid injection system of claim 6, further comprising a sealed member for enclosing the connection port of the at least one fluid container and the first end of the multi-use fluid path set.

10. A fluid path set assembly comprising:
a plurality of separable single-use fluid path sets connected in a series to define a fluid path extending from a first single-use fluid path set to a last single-use fluid path set, each of the plurality of single-use fluid path sets having a first end and a second end,
wherein the first end of each single-use fluid path set is configured for fluidly connecting to the patient delivery line when any of the plurality of single-use fluid path sets is the first single-use fluid path set in the series of single-use fluid path sets, and
wherein the second end of the last single-use fluid path set is configured for fluidly connecting to a fluid injector.

11. The fluid path set assembly of claim 10, wherein the second end of each of the plurality of single-use fluid path sets has a removable cap.

12. The fluid path set assembly of claim 10, wherein the second end of the first single-use fluid path set is removable to expose a first end of a second single-use fluid path set.

* * * * *